United States Patent
Yanagita et al.

(10) Patent No.: US 8,440,983 B2
(45) Date of Patent: May 14, 2013

(54) RADIATION IMAGE CONVERSION PANEL, ITS MANUFACTURING METHOD, AND X-RAY RADIOGRAPHIC SYSTEM

(75) Inventors: Takafumi Yanagita, Hachioji (JP); Tadashi Arimoto, Hino (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 692 days.

(21) Appl. No.: 12/450,242

(22) PCT Filed: Feb. 22, 2008

(86) PCT No.: PCT/JP2008/053053
§ 371 (c)(1),
(2), (4) Date: Sep. 18, 2009

(87) PCT Pub. No.: WO2008/117600
PCT Pub. Date: Oct. 2, 2008

(65) Prior Publication Data
US 2010/0034351 A1 Feb. 11, 2010

(30) Foreign Application Priority Data

Mar. 27, 2007 (JP) ................................. 2007-081250
Jul. 31, 2007 (JP) ................................. 2007-198698

(51) Int. Cl.
*G01J 1/58* (2006.01)
*G01T 1/00* (2006.01)

(52) U.S. Cl.
USPC .................. 250/458.1; 250/361 R; 250/483.1; 250/473.1; 250/486.1

(58) Field of Classification Search ............... 250/487.1, 250/488.1, 473.1, 483.1, 486.1, 361 R, 458.1, 250/459.1, 580, 581, 472.1
See application file for complete search history.

(56) References Cited

U.S. PATENT DOCUMENTS

| 3,859,527 A | 1/1975 | Luckey |
| 4,947,046 A | 8/1990 | Kawabata et al. |
| 2004/0195514 A1* | 10/2004 | Nagano .................... 250/370.11 |

(Continued)

FOREIGN PATENT DOCUMENTS

| JP | 55-012144 A | 1/1980 |
| JP | 61-142497 A | 6/1986 |

(Continued)

OTHER PUBLICATIONS

Japanese Office Action mailed Jul. 10, 2012 in Japanese Application No. 2009-506248.

(Continued)

*Primary Examiner* — David Porta
*Assistant Examiner* — Yara Green
(74) *Attorney, Agent, or Firm* — Holtz Holtz Goodman & Chick PC

(57) ABSTRACT

Disclosed are a radiation image conversion panel, which provides high luminance, an image without white or black defects, an image free from cracks and an image with reduced unevenness, and its manufacturing method. Also disclosed is an X-ray radiographic system employing the radiation image conversion panel. The radiation image conversion panel of the invention comprises a substrate and provided thereon, a reflection layer, a phosphor layer and a protective layer in that order, wherein the phosphor layer is composed of a phosphor crystal in the form of column, and the reflection layer is formed by vapor phase deposition of two or more kinds of metals.

10 Claims, 2 Drawing Sheets

U.S. PATENT DOCUMENTS

| | | |
|---|---|---|
| 2005/0077480 A1* | 4/2005 | Kishinami et al. .......... 250/484.4 |
| 2006/0033031 A1* | 2/2006 | Takeda et al. ............. 250/370.11 |
| 2006/0038131 A9* | 2/2006 | Homme et al. ........... 250/370.11 |

FOREIGN PATENT DOCUMENTS

| | | |
|---|---|---|
| JP | 61-142500 A | 6/1986 |
| JP | 62-039737 A | 2/1987 |
| JP | 62-110200 A | 5/1987 |
| JP | 4-309897 A | 11/1992 |
| JP | 2004-163383 A | 6/2004 |
| JP | 2004-163410 A | 6/2004 |
| JP | 2005-072148 A | 3/2005 |
| JP | 2006-133126 A | 5/2006 |

OTHER PUBLICATIONS

Japanese Office Action (Notification of Reasons for Refusal) (including an English-language translation thereof) mailed on Mar. 12, 2013 for Japanese Patent application No. 2009-506248.

* cited by examiner

RADIATION IMAGE CONVERSION PANEL, ITS MANUFACTURING METHOD, AND X-RAY RADIOGRAPHIC SYSTEM

This application is the United States national phase application of International Application PCT/JP2008/053053 filed Feb. 22, 2008.

FIELD OF THE INVENTION

The present invention relates to a radiation image conversion panel, its manufacturing method, and an X-ray radiographic system employing the radiation image conversion panel.

TECHNICAL BACKGROUND

Radiographic images such as X-ray images are employed in many fields, for example, for use in diagnosis of an illness. There have been employed, as a method for obtaining X-ray images, so-called radiation photography systems in which X-rays which have passed through an object are irradiated onto a phosphor layer (fluorescent screen) to form a visible light, which is irradiated onto a silver halide photographic material (hereinafter, also denoted simply as a photographic material) similarly to conventional photography, followed by being subjected to photographic processing to obtain a visible silver image.

Recently, there has been disclosed a new method for obtaining an image directly from a phosphor layer in place of an image forming method by use of silver halide photographic materials. In such a method, radiation having passed through an object is absorbed by a phosphor and then, the phosphor is excited by light or heat energy, whereby a radiation energy accumulated in the phosphor through the absorption is radiated as fluorescence and this fluorescence is detected to form an image. Specifically, there is known a radiation image conversion method employing stimulable phosphors, as described in, for example, U.S. Pat. No. 3,859,527 and Japanese Patent O.P.I. Publication No. 55-12144. In this method is used a radiation image conversion panel having a phosphor layer containing a stimulable phosphor. Radiation having passed through an object is irradiated onto the stimulable phosphor layer, in which radiation energy corresponding to radiation transmission densities of the individual portions of the object is accumulated, thereafter, the stimulable phosphor is excited in time series by an electromagnetic wave (exciting light) such as a visible ray or an infrared ray, whereby the radiation energy accumulated in the stimulable phosphor is emitted in the form of a stimulated luminescence. Signals of the thus emitted luminescence are, for example, photoelectrically converted to obtain electric signals. The thus obtained electric signals are reproduced as a visible image on a recording material such as a photosensitive material or on a display such as a CRT.

The radiation image reproduction as above possesses the advantage that a radiation image with extensive information is obtained through radiation exposure dose far lower than that of conventional radiography of the combination of a conventional radiographic film and an intensifying screen.

Such a radiation image conversion panel using a stimulable phosphor accumulates radiation image data and emits accumulated energy by scanning with an excitation light, so that accumulation of radiation images is again feasible after scanning, enabling repeated use. Thus, conventional radiography consumes radiographic films for every photographing but on the contrary, the radiation image conversion method, which repeatedly uses a radiation image conversion panel, is advantageous in terms of resource protection and economical efficiency.

Further, recent diagnostic image analysis requires a radiation image conversion panel of further enhanced sharpness. There were attempted means for improving sharpness, for example, controlling the shape of the formed stimulable phosphor particles to achieve improvement in sensitivity and sharpness. Such attempts included, for example, a method of using a stimulable phosphor layer formed of fine pseudo-columnar blocks deposited on a substrate having a fine convexoconcave pattern as described in Japanese Patent O.P.I. Publication No. 61-142497.

There were also proposed a method employing a radiation image conversion panel having a stimulable phosphor layer in which cracks between columnar blocks obtained by depositing a stimulable phosphor on a substrate having a micropattern were further developed by being subjected to a shock treatment, as described in Japanese Patent O.P.I. Publication No. 61-142500; a method employing a radiation image conversion panel in which cracking is caused on the surface of a stimulable phosphor layer formed on a substrate to form pseudo-columns (Patent Document 1); and a method employing a stimulable phosphor layer having voids which is formed on the substrate surface through vapor deposition and then subjected to a heat treatment to grow the voids to form cracks (Patent Document 2). There was also proposed a radiation image conversion panel having, on a substrate, a stimulable phosphor layer formed of long and thin columnar crystals exhibiting a given inclination to the vertical line of the substrate (Patent Document 3).

Recently, there was proposed a radiation image conversion panel using a stimulable phosphor comprised of an alkali halide such as CsBr as a main component, and activated by Eu. Specifically, the use of Eu as an activator enabled to render it feasible to achieve enhanced X-ray conversion efficiency which was never realized before.

There is known a radiation image conversion panel providing high luminance and reflecting excitation light or stimulated luminescence, employing, as a substrate, a highly-reflective material such as aluminum.

However, generally, a substrate for manufacturing a radiation image conversion panel has a large area (for example, 100×100 mm or larger), and is thin as compared with the size. When the substrate is supported with a support in a vapor deposition apparatus for deposition of a stimulable phosphor, the substrate sags downwards in the center under its own weight, and therefore, there is problem in that it is difficult to form a uniform stimulable phosphor layer on the substrate.

A radiation image conversion panel providing a radiographic image with high image quality is required in which a stimulable phosphor layer is formed through a combination of a reflection layer formation method, which provides a reflection layer between the substrate and a stimulable phosphor layer to efficiently emit stimulated luminescence from a stimulable phosphor layer, and a columnar structure formation method, which obtains a radiographic image with high sharpness by vapor-depositing a stimulable phosphor in the form of column on a substrate with many fine protrusions, i.e., a method of laminating a reflection layer on a substrate with a convexoconcave surface and providing on the substrate a stimulable phosphor layer comprised of a stimulable phosphor in the form of column.

In view of the above, there is proposed a radiation image conversion panel in which a reflection layer reflecting stimulated luminescence is formed on a convexoconcave surface including wall surface of the convexo portions of a substrate, a stimulable phosphor layer containing a phosphor in the form of column is formed on the reflection layer according to a vapor phase deposition method, and a protective layer is formed on the stimulable phosphor layer, the reflection layer is a laminated layer comprising a metal layer and a transparent thin layer (Patent Document 4).

However, the radiation image conversion panel as proposed above improves image quality to some level, but the improvement is still insufficient. There are problems in a single metal layer that many defects are likely to occur, and defects such as density irregularity unevenness in an image are likely to be produced.

Patent Document 1: Japanese Patent O.P.I. Publication No. 62-39737
Patent Document 2: Japanese Patent O.P.I. Publication No. 62-110200
Patent Document 3: Japanese Patent O.P.I. Publication No. 2-58000
Patent Document 4: Japanese Patent O.P.I. Publication No. 2004-163383

DISCLOSURE OF THE INVENTION

Problems to be Solved by the Invention

The present invention has been made in view of the above. An object of the invention is to provide a radiation image conversion panel, which provides high luminance, an image without white or black defects, an image free from cracks, and an image with reduced unevenness, and its manufacturing method. Another object of the invention is to provide an X-ray radiographic system employing the radiation image conversion panel.

Means for Solving the Above Problems

The above object of the invention can be attained by the following constitution.

1. A radiation image conversion panel comprising a substrate and provided thereon, a reflection layer, a phosphor layer and a protective layer in that order, wherein the phosphor layer is composed of a phosphor crystal in the form of column, and the reflection layer is formed by vapor phase deposition of two or more kinds of metals.

2. The radiation image conversion panel of item 1 above, wherein the reflection layer is composed of two or more layers and at least one layer of the two or more layers is a metal layer containing at least one of aluminum and silver.

3. The radiation image conversion panel of item 1 or 2 above, wherein the thickness of the reflection layer is from 0.01 to 0.5 μm, and the reflection layer comprises an uppermost metal layer containing aluminum or silver and a lowermost metal layer containing at least one of nickel and chromium.

4. The radiation image conversion panel of any one of items 1 through 3 above, wherein the radiation image conversion panel further comprises an organic resin layer with a thickness of from 0.5 to 15 μm as a subbing layer provided on the reflection layer, and the substrate is a flexible substrate.

5. The radiation image conversion panel of any one of items 1 through 4 above, wherein the substrate is composed of a polymer compound selected from polyethylene terephthalate, polyethylene naphthalate, polyethylene sulfide and polyimide.

6. The radiation image conversion panel of any one of items 1 through 5 above, wherein the phosphor is a stimulable phosphor.

7. The radiation image conversion panel of any one of items 1 through 6 above, wherein the phosphor is a phosphor containing CsBr as a main component.

8. A method of manufacturing the radiation image conversion panel of any one of items 1 through 7 above, the method comprising the step of forming the phosphor layer according to a vapor phase deposition method.

9. An X-ray radiographic system in which the radiation image conversion panel of any one of items 1 through 7 above is placed in a portable vessel, X-ray irradiation is conducted, and readout is conducted.

Effects of the Invention

The constitution as described above of the invention can provide a radiation image conversion panel, which provides high luminance, an image without white or black defects, an image free from cracks, and an image with reduced unevenness and its manufacturing method, and can provide an X-ray radiographic system employing the radiation image conversion panel.

Figure 1A:
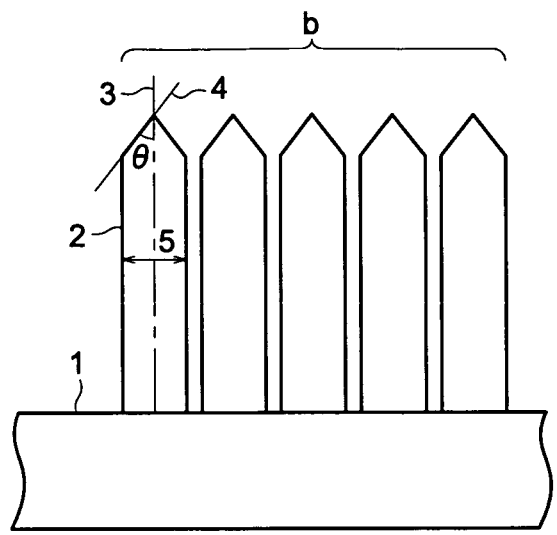
FIGS. 1a and 1b each are a schematic diagram showing one example of shapes of column crystals formed on a substrate.

| EXPLANATION OF THE NUMERICAL NUMBERS | |
|---|---|
| 1: | Substrate |
| 2: | Column crystals |
| 3: | Centerline passing through the center in the direction of crystal growth |
| 4: | Tangent line to the tip section of crystals |
| 5: | Crystal diameter of column crystals |
| 15: | Substrate supporting member |
| 16: | Stimulable phosphor vapor stream |
| 21: | Radiation generating apparatus |
| 22: | Object |
| 23: | Radiation image conversion panel |
| 24: | Stimulable excitation light source |
| 25: | Photoelectric conversion apparatus |
| 26: | Image reproduction apparatus |
| 27: | Image display apparatus |
| 28: | Filter |
| 130: | Heat insulating material |
| 140: | Stimulable phosphor material |
| 150: | Crucible |
| 160: | Vacuum chamber (of a vapor deposition apparatus) |

PREFERRED EMBODIMENT OF THE INVENTION

The radiation image conversion panel of the invention is characterized in that it is a radiation image conversion panel comprising a substrate and provided thereon, a reflection layer, a phosphor layer and a protective layer in that order, wherein a phosphor constituting the phosphor layer forms a crystal in the form of column and the reflection layer is formed by vapor phase deposition of two or more kinds of metals. This is a characteristic in common of the invention regarding items 1 to 9 above.

Next, the invention, its constitution, the preferred embodiments of the invention will be explained in detail.

[Substrate]

As a substrate used in the radiation image conversion panel of the invention, there are mentioned various types of glasses, polymer materials, and metals. Examples thereof include sheet glasses such as quartz, borosilicate glass and chemically reinforced glass; a polymer film; metallic sheets such as an aluminum sheet, an iron sheet and a copper sheet; and a metallic sheet having a metal oxide coating layer. Among these, a polymer film is especially preferred.

As the polymer film used in the invention, a polymer film (plastic film) such as a cellulose acetate film, a polyethylene naphthalate (PEN) film, a polyethylene sulfide film, a polyester film, a polyethylene terephthalate film, a polyamide film, a polyimide (PI) film, a triacetate film, a polycarbonate film or carbon fiber reinforced resin sheet can be used. When column crystals are formed via a vapor-phase deposition method, a polymer film comprising a polymer selected from polyethylene terephthalate, polyethylene naphthalate (PEN), polyethylene sulfide or polyimide (PI) is especially preferred in view of heat resistance.

It is preferred that the substrate in the invention is made of a flexible polymer film having a thickness of from 50 to 500 μm.

The term "flexible substrate" herein implies a substrate wherein the modulus of elasticity (E120) at 120° C. is in the range of from 1000 to 6000 N/mm$^2$. As such a substrate, a polymer film containing polyimide or polyethylene naphthalate is preferred.

The term "modulus of elasticity" corresponds to the inclination of stress relative to strain in an area wherein the strain indicated by the marked line of a sample in conformity to the JIS-C2318 and the stress corresponding thereto exhibit a linear relation, using an tension-tester. This corresponds to the value called "Young's modulus". In the present invention, this Young's modulus is defined as modulus of elasticity.

In the substrate used in the present invention, the modulus of elasticity (E120) is preferably in the range of from 1000 to 6000 N/mm$^2$ at 120° C., and more preferably in the range of from 1200 to 5000 N/mm$^2$ at 120° C., as described above.

Typical examples thereof include a polymer film composed of polyethylene naphthalate (E120=4100 N/mm$^2$), polyethylene terephthalate (E120=1500 N/mm$^2$), polybutylene naphthalate (E120=1600 N/mm$^2$), polycarbonate (E120=1700 N/mm$^2$), syndiotactic polystyrene (E120=2200 N/mm$^2$), polyether imide (E120=1900 N/mm$^2$); polyarylate (E120=1700 N/mm$^2$), polysulfone (E120=1800 N/mm$^2$) and polyether sulfone (E120=1700 N/mm$^2$).

These may be used alone or in a laminated or mixed form. Among these, a polymer film containing polyimide or polyethylene naphthalate is especially preferred.

[Reflection Layer]

The reflection layer in the invention is characterized in that it is formed by vapor phase deposition of two or more kinds of metals. The reflection layer is a layer to reflect the luminescence emitted from the phosphor and to increase the light extraction efficiency, and is a laminate layer composed of two or more layers in view of reflection property or defect prevention. The laminate layer provides high reflection efficiency, greatly minimizes defects such as flaking of layer, and improves resistance to scratching, resulting in improved reliability.

The reflection layer is preferably formed from a material (simple substance of metal, metal alloy, etc.) including any element selected from the group of aluminum (Al), silver (Ag), chromium (Cr), copper (Cu), nickel (Ni), titanium (Ti), magnesium (Mg), rhodium (Rh), platinum (Pt) and gold (Au). Especially, a thin metallic film made up of the aforementioned element such as Ag film and Al film is preferably used. Aluminum (Al), silver (Ag), chromium (Cr) or nickel (Ni) is especially preferred.

The thickness of the reflection layer is preferably from 0.01 to 0.5 μm (10 to 500 nm), and more preferably from 0.01 to 0.3 μm. The reflection layer is preferably formed according to a vapor deposition method or a sputtering method.

It is preferred that in the reflection layer having a thickness of from 0.01 to 0.5 μm, an uppermost layer is a metal layer containing at least one of aluminum (Al) and silver (Ag) and a lowermost layer is a metal layer containing at least one of nickel (Ni) and chromium (Cr).

[Subbing Layer]

It is preferred in the invention that an organic resin layer is provided as a subbing layer between the substrate and the phosphor layer in view of adhesion and the like. The organic resin layer preferably contains a polymer binder (binder), a dispersant, a colorant and the like. The thickness of the organic resin layer is preferably from 0.5 to 15 μm in view of sharpness or heat application, and more preferably from 1 to 10 μm.

Next, the constitution of the subbing layer or the organic resin layer will be explained.

<Polymer Binder>

The subbing layer in the invention is preferably formed by coating and drying of a polymer binder (hereinafter also referred to as a binder) dissolved or dispersed in a solvent. Typical examples of the polymer binder include polyurethane, vinyl chloride copolymer, vinyl chloride-vinyl acetate copolymer, vinyl chloride-vinylidene chloride copolymer, vinyl chloride-acrylonitrile copolymer, butadiene-acrylonitrile copolymer, polyamide resin, polyvinyl butyral, polyester, cellulose derivative (nitrocellulose, etc.), styrene-butadiene copolymer, various kinds of synthetic rubber resins, phenol resin, epoxy resin, urea resin, melamine resin, phenoxy resin, silicon resin, acryl based resin, and urea-formaldehyde resin. Among these, polyurethane, polyester, vinyl chloride copolymer, polyvinyl butyral or nitrocellulose is preferably utilized.

As the polymer binder in the invention, polyurethane, polyester, vinyl chloride copolymer, polyvinyl butyral or nitrocellulose is preferred in view of its adhesion with a phosphor layer. The polymer binder in the invention is preferably one having a glass transition temperature of from 30 to 100° C. in view of its adhesion with crystals to be vapor deposited. The polymer binder polyester is especially preferred in that point.

Examples of a solvent used to form the organic resin layer include a lower alcohol such as methanol, ethanol, n-propanol or n-butanol; a chlorine atom-containing hydrocarbon such as methylene chloride or ethylene chloride; a ketone such as acetone, methyl ethyl ketone or methyl isobutyl ketone; an aromatic compound such as toluene, benzene, cyclohexane, cyclohexanone, or xylene; an ester of a lower fatty acid and a lower alcohol such as methyl acetate, ethyl acetate or butyl acetate; an ether such as dioxane, ethylene glycol monoethyl ether or ethylene glycol monomethyl ether; and a mixture thereof.

The subbing layer may contain pigments or dyes in order to minimize scattering of luminescence emitted from a phosphor layer to improve sharpness.

[Phosphor Layer]

As a phosphor used to form the phosphor layer in the invention, known various kinds of phosphors can be utilized. In the invention, the phosphor is preferably a stimulable phosphor. The phosphor layer is preferably formed according to a vapor-phase deposition method.

Next, typical example of the stimulable phosphor layer in the invention will be explained referring to figures.

Figure 1B:
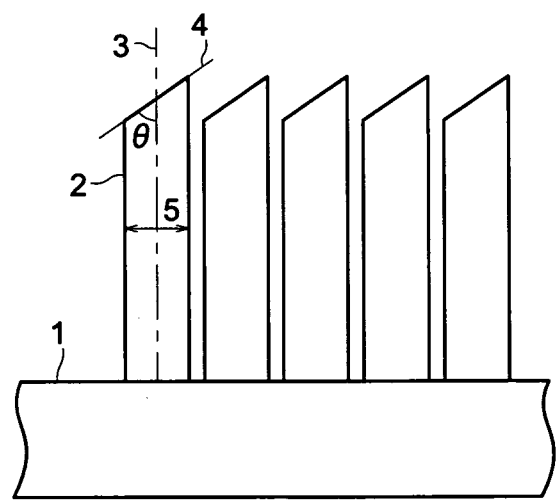

FIGS. 1a and 1b each are a schematic diagram showing examples of shapes of column crystals formed on a substrate. In FIGS. 1a and 1b, numeral 2 designates column crystals of a stimulable phosphor, which has been formed on a substrate 1 via a vapor phase deposition method. At the top of the column crystals, symbol θ, designating an angle formed between a centerline 3 passing through the center in the direction of crystal growth and a tangent line 4 to the top surface, is preferably from 20 to 80 degrees, and more preferably from 40 to 80 degrees. FIG. 1a shows one example of column crystals having an acute site substantially on the center of the top surface. FIG. 1b shows one example of column crystals having an inclined top surface the end of which has an acute site.

Further, in the present invention, the column crystals have an average crystal diameter of preferably from 0.5 to 50 μm, and more preferably from 1 to 10 μm. When the column crystals have an average crystal diameter falling within the range described above, a haze ratio of stimulable phosphor layer b can be reduced, resulting in enhanced sharpness. Herein, the average crystal diameter of the column crystals refers to an average of a diameter of a circle having an area equivalent to the sectional area of each of the column crystals vertical to the substrate, and can be determined from an electron microscope photograph including at least 100 column crystals.

The diameter of the column crystals is affected by the temperature of a substrate, the degree of vacuum, or the incident angle of vapor stream, and therefore, column crystals with a desired diameter can be prepared by controlling these factors. A lower temperature of a substrate tends to render the crystals thinner but excessively low temperature makes it difficult to maintain the column form. The temperature of a substrate is preferably from 50 to 300° C., and more preferably from 150 to 200° C. The incident angle of the vapor stream is preferably from 0 to 50°, and the degree of vacuum is preferably not more than 0.5 Pa.

[Vapor Phase Deposition Method]

Examples of the stimulable phosphors usable in the stimulable phosphor layer formed according to a vapor phase deposition method (also referred to as vapor phase growth process) in the present invention include a phosphor represented by $BaSO_4:A_x$, as described in Japanese Patent O.P.I. Publication No. 48-80487; a phosphor represented by $MgSO_4:A_x$, as described in Japanese Patent O.P.I. Publication No. 48-80488; a phosphor represented by $SrSO_4:A_x$, as described in Japanese Patent O.P.I. Publication No. 48-80489; phosphors such as $Na_2SO_4$, $CaSO_4$ or $BaSO_4$ each added with at least one of Mn, Dy and Tb, as described in Japanese Patent O.P.I. Publication No. 51-29889; phosphors such as BeO, LiF, $MgSO_4$ and $CaF_2$, as described in Japanese Patent O.P.I. Publication No. 52-30487; phosphors such as $Li_2B_4O_7$:Cu, Ag, as described in Japanese Patent O.P.I. Publication No. 53-39277; phosphors such as $Li_2O.(Be_2O_2)$:Cu,Ag, as Japanese Patent O.P.I. Publication No. 54-47883; and phosphors such as SrS:Ce,Sm, SrS:Eu,Sm, $La_2O_2S$:Eu,Sm and (Zn, Cd)S: $Mn_x$ as described in U.S. Pat. No. 3,859,527.

There are also cited ZnS:Cu,Pb phosphor, barium aluminate phosphors represented by general formula, $BaO.xAl_2O_3$: Eu, and alkaline earth metal silicate type phosphors represented by general formula, $M(II) O.xSiO_2$:A, as described in Japanese Patent O.P.I. Publication No. 55-12142.

There are further cited an alkaline earth fluorohalide phosphor represented by formula $(Ba_{1-x-y}Mg_xCa_y)F_x:Eu^{2+}$ as described in Japanese Patent O.P.I. Publication No. 55-12143; a phosphor represented by formula: LnOX:xA, as described in Japanese Patent O.P.I. Publication No. 55-12144; a phosphor represented by formula $(Ba_{1-x}M(II)_x)$ $F_x$:yA, as described in Japanese Patent O.P.I. Publication No. 55-12145; a phosphor represented by formula BaFX:xCe, yA, as described in Japanese Patent O.P.I. Publication No. 55-84389; a rare earth element-activated divalent metal fluorohalide phosphor represented by formula M(II) FX-xA:yLn, as described in Japanese Patent O.P.I. Publication No. 55-160078; a phosphor represented by formula ZnS:A, CdS: A, (Zn, Cd)S:A,X; a phosphor as described in Japanese Patent O.P.I. Publication No. 59-38278, which is represented by the following formula, Formula $xM_3(PO_4)_2.NX_2$:yA or $xM_3(PO_4)_2$:yA, a phosphor as described in Japanese Patent O.P.I. Publication No. 59-155487, which is represented by the following formula, Formula $nReX_3.mAX'_2$:xEu or $nReX_3.mAX'_2$: XEu,ySm;

an alkali halide phosphor as described in Japanese Patent O.P.I. Publication No. 61-72087, which is represented by the following formula, $M(I) X.aM(II).X'_2.bM(III)X''_3$:cA; and a bismuth-activated alkali halide phosphor as described in Japanese Patent O.P.I. Publication No. 61-228400, which is represented by formula of M(I)X:xBi. Alkali halide phosphors are especially preferred, since a stimulable phosphor layer composed of column crystals are easily formed via a vapor deposition method or a sputtering method.

In the invention, a stimulable phosphor represented by the following formula (1) is also preferred.

$M^1X.aM^2X'_2$:eA,A"     Formula (1)

In Formula (1), $M^1$ represents at least one alkali metal atom selected from the group consisting of Li, Na, K, Rb and Cs; $M^2$ represents a divalent metal selected from the group consisting of Be, Mg, Ca, Sr, Ba, Zn, Cd, Cu and Ni; X and X' each represent at least one halogen atom selected from the group consisting of F, Cl, Br and I; A and A" each represent at least one rare earth element selected from the group consisting of Eu, Tb, In, Ce, Tm, Dy, Pr, Ho, Nd, Yb, Er, Gd, Lu, Sm, and Y; "a" satisfies $0 \leq a \leq 0.5$; and "e" satisfies $0 < e \leq 0.2$.

In the stimulable phosphor represented by formula (1) above, $M^1$ represents at least one alkali metal atom selected from the group consisting of Li, Na, K, Rb and Cs, preferably at least one alkali metal atom selected from Rb and Cs atoms, and more preferably a Cs atom.

$M^2$ represents a divalent metal selected from the group consisting of Be, Mg, Ca, Sr, Ba, Zn, Cd, Cu and Ni, and preferably a divalent metal selected from the group consisting of Be, Mg, Ca, Sr, and Ba.

$M^3$ represents a trivalent metal selected from the group consisting of Sc, Y, La, Ce, Pr, Nd, Pm, Sm, Eu, Gd, Tb, Dy, Ho, Er, Tm, Yb, Lu, Al, Ga, and In. Of these, a trivalent metal selected from the group consisting of Y, Ce, Sm, Eu, Al, La, Gd, Lu, Ga and In is preferred.

A represents at least one metal selected from the group consisting of Eu, Tb, In, Ga, Ce, Tm, Dy, Pr, Ho, Nd, Yb, Er, Gd, Lu, Sm, Y, Tl, Na, Ag, Cu and Mg.

X, X' and X" each represent at least one halogen atom selected from the group consisting of F, Cl, Br and I, in enhancing luminance of stimulated luminescence emitted from a stimulable phosphor, preferably at least one halogen atom selected from F, Cl, and Br, and more preferably at least one halogen atom selected from Br and I.

In formula (1), "b" satisfies $0 \leq b < 0.5$, and preferably $0 \leq b \leq 10^{-2}$.

The stimulable phosphor represented by formula (1) can be manufactured, for example, according to the following manufacturing process. As phosphor raw material, compounds described in the following (a), (b) or (c) are used.

(a) One or two or more kinds of compounds selected from the group consisting of NaF, NaCl, NaBr, NaI, KF, KCl, KBr, KI, RbF, RBCl, RbBr, RbI, CsF, CsCl, CsBr and CsI (b) One or two or more kinds of compounds selected from the group consisting of $MgF_2$, $MgCl_2$, $MgBr_2$, $MgI_2$, $CaF_2$, $CaCl_2$, $CaBr_2$, $CaI_2$, $SrF_2$, $SrCl_2$, $SrBr_2$, $SrI_2$, $BaF_2$, $BaCl_2$, $BaBr_2$, $BaBr_2 \cdot 2H_2O$, $BaI_2$, $ZnF_2$, $ZnCl_2$, $ZnBr_2$, $ZnI_2$, $CdF_2$, $CdCl_2$, $CdBr_2$, $CdI_2$, $CuF_2$, $CuCl_2$, $CuBr_2$, $CuI$, $NiF_2$, $NiCl_2$, $NiBr_2$ and $NiI_2$ (c) Compounds having a metal atom selected from atoms such as Eu, Tb, In, Cs, Ce, Tm, Dy, Pr, Ho, Nd, Yb, Er, Gd, Lu, Sm, Y, Tl, Na, Ag, Cu and Mg In the compound represented by formula (1), "a" satisfies $0 \leq a < 0.5$, and preferably $0 \leq a < 0.01$; "b" satisfies $0 \leq b < 0.5$, and preferably $0 \leq b \leq 10^{-2}$; and "e" satisfied $0 < e \leq 0.2$, and preferably $0 < e \leq 0.1$.

Phosphor raw materials, which are selected from the compounds listed in (a) to (c) above, are weighed so as to have a mixture composition meeting the numerical range, and mixed sufficiently employing a mortar, a ball mill or a mixer mill.

Subsequently, the resulting phosphor raw material mixture is introduced into a heat-resistant vessel such as a quartz crucible or an alumina crucible and then placed in an electric furnace to be calcined.

The calcination temperature is suitably from 200 to 1000° C. The calcination time, although it depends on a charging amount of raw materials, calcination temperature and the like, is generally from 0.5 to 6 hours.

As a calcination atmosphere is preferred a weakly reducing atmosphere such as a nitrogen gas atmosphere containing a small amount of hydrogen gas or a carbon dioxide atmosphere containing a small amount of carbon monoxide, a neutral atmosphere such as a nitrogen gas atmosphere or an argon gas atmosphere, or a weakly oxidizing atmosphere containing a small amount of oxygen.

After completion of calcination under the foregoing condition, calcined material is removed from the electric furnace and subjected to pulverization. Thereafter, powdery calcined material is again introduced into a heat resistant vessel and then placed in an electric furnace to be re-calcined under the foregoing condition. This re-calcination is preferred in further enhancing emission luminance of phosphor.

When the calcined material is cooled from calcination temperature to room temperature, an intended phosphor can be obtained by removing the calcined material from an electric furnace and allowing it to stand in an aerial atmosphere. In this regard, the calcined material may be cooled at the same atmosphere as the atmosphere in the calcination such as a weakly reducing atmosphere or neutral atmosphere.

Alternatively, the calcined material is moved from a heating section to a cooling section within the electric furnace, and rapidly cooled in a weakly reducing atmosphere, a neutral atmosphere or a weakly oxidizing atmosphere, thereby leading to further enhanced stimulated luminescence luminance of phosphor.

The present invention is effective and can provide the same effect as above in an ordinary phosphor crystal in the form of column having no stimulated luminescence, for example, CsI:Tl.

It is a feature in the invention that a stimulable phosphor layer is formed via a vapor phase growth process.

Examples of the vapor growth process for the stimulable phosphor include a vapor deposition method, a sputtering method, a CVD method, an ion plating method and the like.

In the invention, the following methods are mentioned.

The vapor deposition method as a first method will be explained below.

After a substrate is placed in a vapor deposition apparatus, the inside of the apparatus is evacuated to a vacuum degree of $1.333 \times 10^{-4}$ Pa.

Subsequently, an argon gas or a nitrogen gas is preferably introduced into the apparatus to obtain an intended degree of vacuum. The degree of vacuum is preferably from $1.0 \times 10^{-3}$ to 1.0 Pa. At least one of stimulable phosphors described above is heated and evaporated employing a resistance heating method or an electron-beam method, whereby a stimulable phosphor grows on the substrate surface to a desired thickness. As a result, a stimulable phosphor layer containing no binder is formed. It is also possible that the evaporation process is carried out plural times to form a stimulable phosphor layer.

In this evaporation process, it is also possible that co-deposition is performed employing plural resistance heaters or electron beams to prepare an intended stimulable phosphor on the substrate and at the same time form a stimulable phosphor layer.

It is preferred that the radiation image conversion panel of the present invention is manufactured by forming a protective layer on the side of the substrate opposite the stimulable phosphor layer thereon after completion of the deposition, as necessary. A procedure may be carried out in which a substrate is provided after forming a stimulable phosphor layer on a protective layer.

Further, in the deposition method, a material (a substrate, a protective layer or an intermediate layer) to be deposited thereon may be cooled or heated during deposition, as necessary.

After completion of the deposition, the stimulable phosphor layer may be subjected to a heating treatment. Reactive deposition may also be conducted in which deposition is carried out while introducing a gas such as $O_2$ or $H_2$ in the vapor deposition method above.

The sputtering method as a second method will be explained below.

After a substrate with a protective layer or an intermediate layer is placed in a sputtering apparatus in the same manner as in the deposition method above, the inside of the apparatus is once evacuated to a vacuum degree of $1.333 \times 10^{-4}$ Pa, and then, an inert gas such as Ar or Ne as a gas for sputtering is introduced into the apparatus to give a vacuum degree of 0.01 Pa. Subsequently, sputtering is carried out employing the stimulable phosphor as a target to form a stimulable phosphor layer with an intended thickness on the substrate.

Similarly to the vapor deposition method, various kinds of application treatments are usable in the sputtering method.

There are provided a CVD method as a third method and an ion plating method as a fourth method.

Further, the vapor phase growth speed of the stimulable phosphor layer in the foregoing vapor phase growth is preferably from 0.05 to 300 μm/min. A vapor phase growth speed of less than 0.05 μm/min lowers productivity of the radiation image conversion panel of the invention, which is undesired. In contrast, a vapor phase growth speed exceeding 300 μm/min is difficult to control the growth speed.

When radiation image conversion panels are prepared by the vacuum deposition method, the sputtering method and the like described above, the content of the stimulable phosphor in the stimulable phosphor layer can be increased because of absence of binders, whereby radiation image conversion panels can be manufactured which are preferred in view of sensitivity and resolution.

The thickness of the stimulable phosphor layer depends on the intended use of a radiation image conversion panel or on kinds of stimulable phosphors used, but it is preferably from 50 μm to 1 mm in view of producing effects of the present invention, more preferably from 100 to 600 μm, and still more preferably from 100 to 400 μm.

When a stimulable phosphor layer is formed via the above-described vapor phase growth method, the temperature of a substrate on which a stimulable phosphor layer is to be formed is preferably at least 100° C., more preferably at least 150° C., and still more preferably 150 to 400° C.

The stimulable phosphor layer of the radiation image conversion panel of the present invention is preferably formed on a substrate according to vapor phase growth of a stimulable phosphor represented by formula (1), and it is preferred that the stimulable phosphor forms a phosphor crystal in the form of column during its layer formation.

In order to form a stimulable phosphor layer composed of a phosphor crystal in the form of column via a method such as a vapor deposition method or a sputtering method, the compounds (stimulable phosphors) represented by formula (1) are utilized, but of these, a CsBr based phosphor is preferably utilized.

In the present invention, it is preferred that the phosphor with column crystal structure columnar comprises a stimulable phosphor represented by the following formula (2) as a main component.

CsX:A  Formula (2)

In formula (2), X is Br or I; and A is Eu, In, Tb or Ce.

In the invention, the phosphor comprising CeBr as a main component is preferred in view of luminance and storage stability.

In a method of forming a phosphor layer on a substrate via a vapor phase deposition method, vapor or the raw material of a stimulable phosphor is supplied on the substrate to cause vapor phase growth, whereby a stimulable phosphor layer is formed which is composed of column crystals separated from each other.

In such a case, it is preferred that the shortest distance between the substrate and a crucible charged with a stimulable phosphor is usually set to from 10 to 60 cm, suiting the average range of the stimulable phosphor vapor.

The stimulable phosphor as a vaporization material, after molded by pressing or hot pressing or uniformly melted, is placed in the crucible. Degassing treatment is preferably conducted on this occasion. Though the vaporization of the stimulable phosphor is carried out by scanning with an electron beam generated from an electron gun, the vaporization may be performed by another method.

The vaporization material may be a single stimulable phosphor or an admixture of different stimulable phosphor materials.

The stimulable phosphor as a main component may be doped with an activator. For example, only RbBr as a main component, after vapor deposited, may be doped with Tl as an activator. The doping is possible even when the thickness of the layer is large, since the crystals are each independent, and MTF is not lowered, since the crystal growth is difficult to occur.

The doping can be performed by thermal diffusion or ion injection of a doping agent (an activator) into the layer of the phosphor as the main component.

The distance between each of column crystals is preferably at most 30 μm, and more preferably at most 5 μm. The distance exceeding 30 μm increases scattering of laser light in the phosphor layer, resulting in lowered sharpness.

[Formation of Stimulable Phosphor Layer]

Next, formation of the stimulable phosphor layer of the present invention will be explained referring to FIG. 2.

Figure 2:
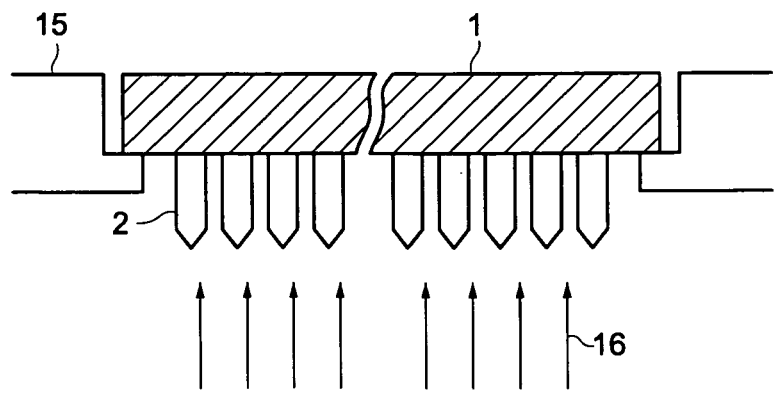
FIG. 2 is a schematic diagram showing one example forming a stimulable phosphor layer on a substrate via vapor deposition.

FIG. 2 illustrates a state forming a stimulable phosphor layer on a substrate via vapor deposition, in which stimulable phosphor vapor stream 16 is applied onto the substrate at an incident angle of 0 to 5° to the line normal to the substrate surface to form column crystals on the substrate.

Since the stimulable phosphor layer thus formed on the substrate contains no binder, it has excellent directionality, resulting in enhanced directionality of stimulable excitation light and stimulated luminescence. This stimulable phosphor layer can provide a thickness thinner than that of a radiation image conversion panel having a dispersion-type stimulable phosphor layer, in which the stimulable phosphor is dispersed in a binder. Moreover, scattering of the stimulable excitation light in the stimulable phosphor layer is reduced, resulting in enhanced sharpness.

Further, the spacing between each of column crystals may be filled with a filler such as a binder to strengthen the phosphor layer. Furthermore, the spacing may be filled with a material with high light absorbance or a material with high reflectance. The presence of such a material is effective in reducing lateral diffusion of stimulable excitation light entering the phosphor layer, in addition to the foregoing strengthening effect.

The material with high reflectance refers to one with a high reflectance with respect to stimulable excitation light (500 to 900 nm, specifically 600 to 800 nm), including metals such as aluminum, magnesium, silver and indium, white pigments and colorants ranging green to red.

Reflectance of the stimulable phosphor layer of the present invention is preferably at least 20% in view of obtaining a radiation image conversion panel exhibiting high sensitivity, more preferably at least 30%, and still more preferably at least 40%. In addition, the upper limit of the reflectance is 100%.

The material exhibiting high reflectance refers to a material with high reflectance with respect to stimulable excitation light (500 to 900 nm, specifically 600 to 800 nm), and preferred examples thereof include aluminum, magnesium, silver, indium and other metals.

In the invention, when a substrate is subjected to mirror-finishing treatment reflecting light (vapor deposition, for example), employing aluminum, reflectance of a stimulable phosphor layer is measured.

The reflectance is measured under the same measuring conditions employing the following measuring apparatus.

Apparatus: HITACHI 1557 type spectrophotometer
(Measuring Condition)
Wavelength of measured light: 680 nm
Scanning speed: 120 nm/min
Number of repetition: 10
Response: Automatic Setting The invention can be applied to various applications of phosphors as well as to a stimulable phosphor. For example, when a phosphor is applied to a scintillator, various phosphor materials known in the art are usable as materials for forming a phosphor layer (also referred to as "a scintillator layer"). In the invention, cesium iodide (CsI) is especially preferred as the phosphor material, since cesium iodide can easily form a phosphor crystal in the form of column through vapor deposition, which minimizes scattering of light emitted in the crystal due to light guide effect, whereby it is possible to increase the thickness of the scintillator layer.

However, since CsI alone results in lower light emission efficiency, various activators are incorporated. One example is listed in which CsI and sodium iodide (NaI) are mixed at any appropriate mol ratio, as described in Japanese Patent Publication No. 54-35060. Further, as disclosed, for example, in Japanese Patent O.P.I. Publication No. 2001-59899, vapor-deposited CsI is preferred which incorporates activators such as thallium (Tl), europium (Eu), indium (In), lithium (Li), potassium (K), rubidium (Rb) and sodium (Na). In the present invention, thallium (Tl) and europium (Eu) are preferred, and thallium (Tl) is more preferred.

In addition, in the present invention, it is preferable to employ, as raw materials, cesium iodide and additives containing at least one kind of thallium compounds. Namely, thallium-activated cesium iodide (Cs:Tl) is preferred since it has a broad luminescence wavelength of from 400 to 750 nm.

Thallium compounds in the additives in the invention containing at least one thallium compound, include various thallium compounds (namely compounds having an oxidation number of +I and +III).

In the present invention, preferred examples of the thallium compounds include thallium bromide (TlBr), thallium chloride (TlCl), and thallium fluorides (TlF and $TlF_3$).

Further, the melting point of the thallium compounds in the present invention is preferably in the range of from 400 to 700° C. When the melting point exceeds 700° C., the additives are non-uniformly located in the columnar crystal, resulting in a decrease in light emission efficiency. Meanwhile, the melting point in the present invention refers to one at ordinary temperature and ordinary pressure.

It is desirable that the content of the aforesaid additives in the phosphor layer in the present invention is optimized depending on its object and performance. The additive content is preferably from 0.001 to 50 mol %, and more preferably from 0.1 to 10.0 mol %, based on the content of cesium iodide.

When the additive content is less than 0.001 mol % based on the content of cesium iodide, the luminance of emitted luminescence results in no significant difference from that obtained by employing cesium iodide alone, whereby it is not possible to realize the targeted luminance. On the other hand, when it exceeds 50 mol %, it is not possible to maintain properties and functions of cesium iodide.

In the present invention, after forming a phosphor layer onto a polymer film via vapor deposition of raw material of phosphor (scintillator), the resulting phosphor layer is preferably subjected to compression/heat treatment through a heated roller of 200 to 440° C., whereby the top surface of the phosphor columnar crystal is planarized.

The above compression/heat treatment makes it possible to heat-treat the phosphor layer surface at a temperature not less than heatproof temperature of a polymer film, whereby luminance is improved in the phosphor layer surface which greatly contributes to sharpness. It is preferred that the temperature of the polymer film as a substrate maintains lowered, whereby damage to the polymer film is minimized. The compression/heat treatment improves uniformity of the phosphor layer surface and graininess, and can provide a scintillator panel which excels in luminance, sharpness and graininess.

[Protective Layer]

It is required that the stimulable phosphor layer in the invention comprises a protective layer.

The protective layer may be formed by coating a coating composition for the protective layer on the stimulable phosphor layer or the protective layer which was previously prepared may be adhered to the substrate. Alternatively, a procedure of forming a stimulable phosphor layer on the protective layer which was previously prepared is also applicable. Materials used for the protective layer include those which are usually used for protective layers. Examples thereof include cellulose acetate, nitrocellulose, polymethyl methacrylate, polyvinyl butyral, polyvinyl formal, polycarbonate, polyester, polyethylene terephthalate, polyethylene, polyvinylidene chloride, nylon, polytetrafluoroethylene, polytrifluoroethylene chloride, copolymer of terafluoroethylene and hexafluoropropylene, copolymer of vinylidene chloride and vinyl chloride, and copolymer of vinylidene chloride and acrylonitrile. Further, a transparent glass substrate may be used as a protective layer. Furthermore, the protective layer may be formed as a deposition layer of inorganic material such as SiC, $SiO_2$, SiN or $Al_2O_3$ by means of a vapor deposition or sputtering method. Furthermore, inorganic material such as SiC, $SiO_2$, SiN, and The thickness of the protective layer is preferably from 0.1 to 2,000 μm.

[Application of Radiation Image Conversion Panel]

The radiation image conversion panel of the invention can be applied to various types of an X-ray radiographic system, and is preferably applied to an X-ray radiographic system, which places the radiation image conversion panel in a portable vessel, conducts X-ray irradiation and conducts readout.

Figure 3:
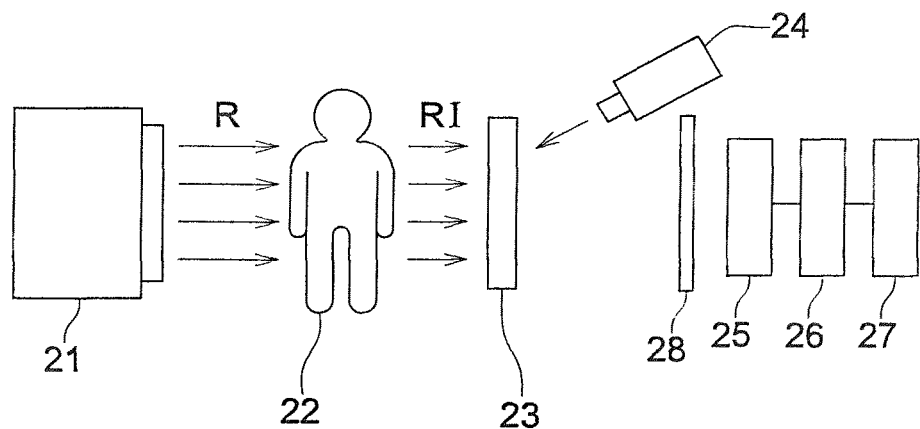
FIG. 3 is a schematic diagram showing one example of the configuration of a radiation image conversion panel and a radiation image reading apparatus.

FIG. 3 illustrates an example of the configuration of the radiation image conversion panel and the radiation image reading apparatus of the present invention.

In FIG. 3, numeral 21 represents a radiation generating apparatus, numeral 22 represents an object, numeral 23 represents a radiation image conversion panel having a visible- or infrared-stimulable phosphor layer, numeral 24 represents a stimulable excitation light source to cause a latent image stored in the radiation image conversion panel 23 to be emitted as stimulated luminescence, numeral 25 represents a photoelectric conversion apparatus to detect the stimulated luminescence emitted from the radiation image conversion panel 23, numeral 26 represents an image reproduction apparatus to reproduce photoelectric conversion signals detected in the photoelectric conversion apparatus 25 as an image, numeral 27 represents an image display apparatus to display the reproduced image, and numeral 28 represents a filter to shield reflection of light emitted from the stimulable excitation light source 24 and to allow only light emitted from the radiation image conversion panel 23 to pass through. FIG. 3 shows an example of obtaining a radiation transmission-type image of an object, and where object 22 itself radiates radiation rays, the radiation generating apparatus 21 is not particularly required.

The photoelectric conversion apparatus 25 and an apparatus downstream the photoelectric conversion apparatus 25 are not specifically limited to those described above, and may be any one which is capable of reproducing light information in the radiation image conversion panel 23 as any image.

As shown in FIG. 3, when object 22 is arranged between radiation generation apparatus 21 and radiation image conversion panel 23, and exposed to radiation R, radiation R passes through respective portions of object 22 in accordance with their radiation transmittance thereof, and the resulting transmission image (also denoted as RI), i.e., an image having different radiation intensities enters radiation image conversion panel 23. The thus entered transmission image RI is absorbed in the stimulable phosphor layer of the radiation image conversion panel 23, in which electrons and/or holes are generated in proportion to the dose of the absorbed radiation and accumulated at a trap level of the stimulable phosphor to form a latent image accumulating energies of the radiation transmission image. Subsequently, the latent image is excited with light energy to form an actual image, i.e., the stimulable phosphor layer is irradiated with the stimulable excitation light source (24) emitting visible or infrared light to eject the electrons and/or holes accumulated on the trap level to emit the accumulated energy as stimulated luminescence. The intensity of the emitted luminescence is proportional to the number of accumulated electrons and/or holes, that is, an energy amount of the radiation absorbed in the stimulable phosphor of the radiation image conversion panel 23. The thus obtained light signals are converted to electric signals by the photoelectric conversion apparatus 25 such as a photomultiplier, which are reproduced as an image by the image reproduction apparatus 26, then displaying the image in the image display apparatus 27. As the image reproduction 26, it is effective to employ one which not only reproduces electric signals as an image but conducts so-called image processing or computation, memory and storage of an image.

On excitation due to light energy, the stimulated luminescence emitted from the stimulable phosphor layer is required to be separated from the reflected light of stimulable excitation light and a photoelectric conversion apparatus to receive the stimulated luminescence emitted from the stimulable phosphor layer has generally higher sensitivity to light in the short wavelength region of 600 nm or shorter. The stimulated luminescence emitted from the stimulable phosphor layer is preferably one having a spectral distribution in the shorter wavelength region. The wavelength of the stimulated luminescence emitted from the stimulable phosphor in the invention falls within the region of from 300 to 500 nm, and that of the stimulable excitation light within the region of from 500 to 900 nm, satisfying the foregoing conditions. Further, along with a recent trend to down-sized diagnostic apparatuses, a semiconductor laser with high output, which is capable of being easily down-sized, is preferred as an excitation light employed to read images in the radiation image conversion panel. The semiconductor laser has a wavelength of 680 nm and the stimulable phosphor used in the radiation image conversion panel of the invention exhibits extremely high sharpness when using an excitation light of 680 nm.

Thus, the stimulable phosphor of the present invention emits luminescence having a main peak at 500 nm or less, which is easily separable from the stimulable excitation light and in accordance with spectral sensitivity of the receiver, leading to enhanced light-receiving efficiency and enhanced sensitivity of an image receiving system.

A light source including the wavelength exciting the stimulable phosphor used in the radiation image conversion panel 23 is used as the stimulable excitation light source 24. Specifically, a laser light simplifies an optical system and increases stimulated luminescence intensity, resulting in preferable performance.

The beam diameter of a laser with which the stimulable phosphor layer of the present invention is irradiated is preferably at most 100 µm, and more preferably at most 80 µm.

Examples of the laser include an He—Ne laser, He—Cd laser, Ar ion laser, Kr laser, $N_2$ laser, YAG laser and its second harmonic wave, ruby laser, semiconductor laser, various dye lasers, and metal vapor lasers such as a copper vapor laser. Of these, continuous oscillation lasers such as an He—Ne laser and an Ar ion laser are usually desirable, and pulse-oscillated lasers are also usable by synchronizing the pulse with a scanning time for one pixel of the panel. In cases when the separation is made employing retard of luminescence emission instead of using filter 28, the use of the pulse-oscillated laser is preferable to modulation of the continuous oscillation laser, as described in Japanese Patent O.P.I. Publication No. 59-22046.

Of the various laser light sources described above, semiconductor lasers are specifically preferred, because they are compact and inexpensive, and do not require a modulator.

Filter 28 allows the stimulated luminescence emitted from the radiation image conversion panel 23 to transmit through and shields stimulable excitation light, and is determined considering a combination of the wavelength of the stimulated luminescence from a stimulable phosphor contained in the radiation image conversion panel 23 and the wavelength of the stimulable excitation light from the stimulable excitation light source 24.

For example, in the preferred practical combination of a stimulable excitation light wavelength of from 500 to 900 nm with a stimulated luminescence wavelength of from 300 to 500 nm, violet to blue glass filters such as C-39, C-40, V-40, V-42 and V-44 (available from TOSHIBA CORP.); 7-54 and 7-59 (available from Corning Co. Ltd.); and BG-1, BG-3, BG-25, BG-37 and BG-38 (available from Spectrofilm Co. Ltd.) are used. When interference filters are used, it is possible to select arbitrarily and use specific filters. The photoelectric conversion apparatus 25 may be any as long as it is one which is capable of converting variation of luminescence energy to that of electric signal such as a photoelectric tube, a photomultiplier tube, a photodiode, a phototransistor, a solar cell and a photoconductive element.

EXAMPLES

Next, the present invention will be explained employing examples, but is not specifically limited thereto.

<<Preparation of Radiation Image Conversion Panel>>

A reflection layer with an intended thickness was provided on a substrate with a size of 100 cm×100 cm adhered to a metal block, employing a target of aluminum, silver, nickel or chromium as shown in Table 1 and a sputtering apparatus. When two kinds of targets are used, one target is exchanged to the other during formation of a protective layer so as to obtain half the thickness of the protective layer from each target. When an alloy protective layer is formed, a target employing two kinds of metals is provided, and subjected to simultaneous sputtering. The materials above are subjected to sputtering treatment to form a protective layer. After that, a solution in which polyester resin is dissolved in methyl ethyl ketone is coated on the protective layer via a spin coater, and dried at 100° C. for 10 hours in a thermostat to form a subbing layer.

Figure 4:
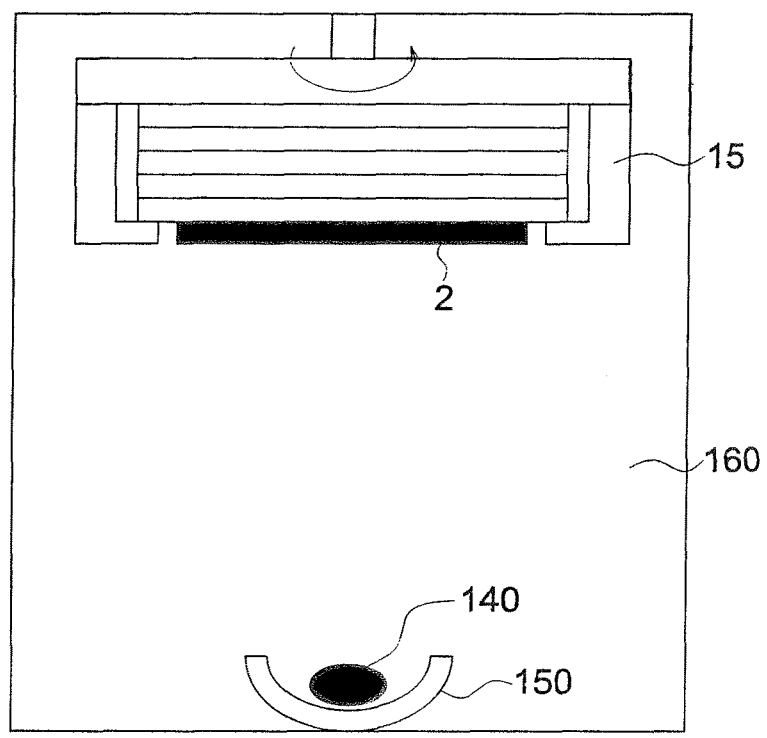
FIG. 4 is a sectional diagram showing structure of one example of a vapor deposition apparatus.

Each of the resulting substrates was adhered to a metal block, placed in the vacuum chamber of a vapor deposition apparatus as shown in FIG. 4. A stimulable phosphor layer composed of a column crystal stimulable phosphor (CsBr:Eu) was formed on each substrate, employing a method as described below.

The substrate obtained above was placed in the vacuum chamber and a phosphor material (CsBr:Eu) as a vapor source was press molded and put into a crucible cooled with water. After that, the vacuum chamber was once evacuated and adjusted to a degree of vacuum of 0.133 Pa by introduction of an argon gas. Subsequently, the temperature (also referred to as substrate temperature) of the subbed substrate with a resin subbed layer was maintained at about 140° C., while the subbed substrate was rotated at a rotation speed of 10 rpm. The resistive heating crucible was heated to vapor deposit the stimulable phosphor onto the substrate to form a stimulable phosphor layer with a thickness of 300 μm. When the thickness reached 300 μm, the deposition was terminated. The resulting stimulable phosphor layer was incorporated in a protective layer envelope in a dry air atmosphere. Thus, a radiation image conversion panel sample with the stimulable phosphor layer tightly sealed, corresponding to an aluminum substrate, was prepared.

<<Evaluation>>

The above-obtained radiation image conversion panel sample was evaluated according to the following method. The results are shown in Table 1.

<<Evaluation of Luminance And Luminance Distribution>>

Luminance was determined employing Regius 190 produced by Konica Minolta MG., Inc. Each of the samples was adhered to the cassette for Regius 190, which was a portable vessel. Each of the radiation image conversion panel samples was exposed to X-rays in a tungsten tube bulb at 80 kVp and 10 mAs at a distance between the radiation source and the panel sample, and the cassette was set within Regius 190 for reading the signals. The resulting data was analyzed, employing a CS-3 software attached to Re Regius 190, and luminance was determined.

<<Evaluation of Image Defects>>

The image obtained above was reproduced on a monitor, and the number of white spots or black spots in the image with a size of 50 mm×50 mm was counted, and evaluated as a measure of image defects.

<<Evaluation of Cracks>>

The sample was adhered to the Regius cassette produced by Konica Minolta MG., Inc., and the resulting material was dropped from 75 cm height 100 times. The image before and after the drop was visually observed and evaluated according to the following criteria:

1: Cracks markedly increase which is not workable.
2: Cracks increase.
3: Cracks increase, which is at a workable level.
4: Few cracks were observed.
5: No cracks were observed.

The results are shown in Table 1.

TABLE 1

| Reflection Layer | | Substrate | | Subbing Layer | | | | | |
|---|---|---|---|---|---|---|---|---|---|
| Kinds | Thickness (μm) | Kinds | Thickness (μm) | Kinds | Thickness (μm) | Luminance | Image Defects | Cracks | Remarks |
| — | — | Al | 1 | — | — | 100 | 53 | 1 | Comp. |
| Al | 0.02 | *PEN | 0.5 | ***PES | 1 | 82 | 80 | 3 | Comp. |
| Ni | 0.02 | PEN | 0.5 | PES | 1 | 55 | 51 | 3 | Comp. |
| Al/Ni | 0.05 | PEN | 0.5 | PES | 1 | 122 | 8 | 4 | Inv. |
| Al | 0.02 | **PIM | 0.5 | PES | 1 | 70 | 69 | 3 | Comp. |
| Ni | 0.02 | PIM | 0.5 | PES | 1 | 49 | 48 | 3 | Comp. |
| Ni—Cr Alloy | 0.05 | PIM | 0.5 | PES | 1 | 52 | 41 | 3 | Comp. |
| Al/Ni | 0.05 | PIM | 0.5 | PES | 1 | 125 | 3 | 5 | Inv. |
| Al/Cr | 0.05 | PIM | 0.5 | PES | 1 | 118 | 6 | 5 | Inv. |
| Al/Ni—Cr Alloy | 0.05 | PIM | 0.5 | PES | 1 | 130 | 4 | 5 | Inv. |
| Al/Ni—Cr Alloy | 0.3 | PIM | 0.5 | PES | 1 | 122 | 3 | 5 | Inv. |
| Al/Ni—Cr Alloy | 0.6 | PIM | 0.5 | PES | 1 | 105 | 18 | 4 | Inv. |
| Al/Ni—Cr Alloy | 0.05 | PIM | 0.5 | — | — | 125 | 11 | 4 | Inv. |
| Al/Ni—Cr Alloy | 0.05 | PIM | 0.5 | PES | 0.6 | 128 | 7 | 5 | Inv. |
| Al/Ni—Cr Alloy | 0.05 | PIM | 0.5 | PES | 3 | 120 | 5 | 5 | Inv. |
| Al/Ni—Cr Alloy | 0.05 | PIM | 0.5 | PES | 8 | 115 | 6 | 5 | Inv. |
| Al/Ni—Cr Alloy | 0.05 | PIM | 0.5 | PES | 12 | 109 | 14 | 4 | Inv. |
| Ag | 0.05 | PIM | 0.5 | PES | 1 | 72 | 72 | 3 | Comp. |
| Ag/Cr | 0.05 | PIM | 0.5 | PES | 1 | 119 | 5 | 5 | Inv. |
| Ag/Ni | 0.05 | PIM | 0.5 | PES | 1 | 127 | 6 | 5 | Inv. |
| Ag/Ni—Cr Alloy | 0.05 | PIM | 0.5 | PES | 1 | 133 | 2 | 5 | Inv. |

Comp.: Comparative, Inv.: Inventive
*PEN: Polyethylene Naphthalate,
**PIM: Polyimide,
***PES: Polyester As is apparent from Table 1, inventive radiation image conversion panel samples provide high luminance, reduced image defects or cracks, and an image free of unevenness, showing superior results.

The invention claimed is:

1. A radiation image conversion panel comprising a substrate and provided thereon, a reflection layer having a thickness of from 0.01 to 0.5 μm, a phosphor layer, and a protective layer in that order, wherein the phosphor layer is composed of a phosphor crystal in the form of a column, and the reflection layer comprises an uppermost metal layer containing a metal selected from the group consisting of aluminum and silver, and a lowermost metal layer containing at least one metal selected from the group consisting of nickel and chromium, the reflection layer being formed by vapor phase deposition of two or more of said metals.

2. The radiation image conversion panel of claim 1, wherein the radiation image conversion panel further comprises an organic resin layer with a thickness of from 0.5 to 15

µm as a subbing layer provided between the phosphor layer and the reflection layer, and the substrate is a flexible substrate.

3. The radiation image conversion panel of claim 1, wherein the substrate is composed of a polymer compound selected from the group consisting of polyethylene terephthalate, polyethylene naphthalate, polyethylene sulfide and polyimide.

4. The radiation image conversion panel of claim 1, wherein the phosphor is a stimulable phosphor.

5. The radiation image conversion panel of claim 1, wherein the phosphor is a phosphor containing CsBr as a main component.

6. A method of manufacturing the radiation image conversion panel of claim 1, the method comprising the step of forming the phosphor layer according to a vapor phase deposition method.

7. An X-ray radiographic system comprising:
a radiation image conversion panel placed in a portable vessel, the panel comprising a substrate and provided thereon, reflection layer having a thickness of from 0.01 to 0.5 µm, a phosphor layer and a protective layer in that order, in which the phosphor layer is composed of a phosphor crystal in the form of a column and the reflection layer comprises an uppermost metal layer containing a metal selected from the group consisting of aluminum and silver, and a lowermost metal layer containing at least one metal selected from the group consisting of nickel and chromium, the reflection layer being formed by vapor phase deposition of two or more of said metals;
an X-ray irradiation apparatus;
a stimulable excitation light source; and
a photoelectric conversion apparatus,
wherein X-ray radiated from the X-ray irradiation apparatus, which has passed through an object, is accumulated in the phosphor of the panel as a transmission image, the accumulated transmission image is excited with excitation light from a stimulable excitation light source to emit stimulated luminescence, and the emitted stimulated luminescence is detected by the photoelectric conversion apparatus.

8. The radiation image conversion panel of claim 1, wherein the phosphor layer comprises CsI.

9. The radiation image conversion panel of claim 8, wherein the CsI has been vapor-deposited, and the vapor-deposited CsI incorporates an activator selected from the group consisting of thallium, europium, indium, lithium, potassium, rubidium and sodium.

10. The radiation image conversion panel of claim 9, wherein the activator is thallium or europium.

* * * * *